United States Patent [19]
Schafer et al.

[11] Patent Number: 5,874,406
[45] Date of Patent: Feb. 23, 1999

[54] SYNTHETIC PEPTIDE ANALOGS OF LUNG SURFACE PROTEIN SP-C

[75] Inventors: Klaus Peter Schafer, Constance; Klaus Melchers, Aach, both of Germany

[73] Assignee: BYK Gulden Lomberg Chemische Fabrik GmbH, Constance, Germany

[21] Appl. No.: 750,194

[22] PCT Filed: May 27, 1995

[86] PCT No.: PCT/EP95/02028

§ 371 Date: Nov. 27, 1996

§ 102(e) Date: Nov. 27, 1996

[87] PCT Pub. No.: WO95/32992

PCT Pub. Date: Dec. 7, 1995

[30] Foreign Application Priority Data

May 31, 1994 [DE] Germany ............................ 44 18 936.2

[51] Int. Cl.$^6$ ..................... C07K 14/785; A61K 38/17
[52] U.S. Cl. .................... 514/12; 514/2; 514/78; 530/324
[58] Field of Search ..................... 530/300, 350, 530/324; 536/23.1, 23.5; 514/2, 12, 78

[56] References Cited

U.S. PATENT DOCUMENTS

| | | | |
|---|---|---|---|
| 5,385,840 | 1/1995 | Benson et al. | 435/325 |
| 5,387,746 | 2/1995 | Whitsett | 514/12 |
| 5,552,161 | 9/1996 | Disse et al. | 424/557 |

FOREIGN PATENT DOCUMENTS

| | | | |
|---|---|---|---|
| 0 119 056 A2 | 9/1984 | European Pat. Off. | A61K 31/685 |
| WO 86/03408 | 6/1986 | WIPO | A61K 37/02 |
| WO 87/06588 | 11/1987 | WIPO | C07K 3/02 |
| WO 91/18015 | 11/1991 | WIPO | C07K 7/10 |

OTHER PUBLICATIONS

Glasser et al. (1988) J. Biol. Chem. 263: 10326–10331.
Longo et al. (1993) Science 261: 453–486.

*Primary Examiner*—David L. Fitzgerald
*Attorney, Agent, or Firm*—Jacobson, Price, Holman & Stern, PLLC

[57] ABSTRACT

Polypeptide analogs of human the human lung surfactant protein, SP-C, are provided. The polypeptides have the following structure:

```
    0   1   2   3   4   5   6   7   8   9  10
(A) Gly Ile Pro  B   B  Pro Val His Leu Lys 11  12  13  14  15  16  17  18  19  20
    Arg Leu Leu Ile Val Val Val Val Val Val 21  22  23  24  25  26  27  28  29  30
    Leu Ile Val Val Val Ile Val Gly Ala Leu 31  32  33  34
    Leu  C  Gly Leu
``` wherein A is H or Phe, B is Phe or Trp, and C is Ile, Leu, or Ser. They exhibit surfactant activity and are useful in the treatment of respiratory distress syndromes in premature infants and adults.

12 Claims, No Drawings

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 35 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Peptide
        ( B ) LOCATION:1
        ( D ) OTHER INFORMATION:/note= "Xaa is Phe or not an amino acid"

( i x ) FEATURE:
        ( A ) NAME/KEY: Peptide
        ( B ) LOCATION:5
        ( D ) OTHER INFORMATION:/note= "Xaa is Phe or Trp"

(ix) FEATURE:
  (A) NAME/KEY: Peptide
  (B) LOCATION:6
  (D) OTHER INFORMATION:/note= "Xaa is Phe or Trp"

(ix) FEATURE:
  (A) NAME/KEY: Peptide
  (B) LOCATION:33
  (D) OTHER INFORMATION:/note= "Xaa is Ile, Leu or Ser"

(xi) SEQUENCE DESCRIPTION: SEQ ID NO: 1:

Xaa Gly Ile Pro Xaa Xaa Pro Val His Leu Lys Arg Leu Leu Ile Val
1               5                   10                  15

Val Val Val Val Val Leu Ile Val Val Val Ile Val Gly Ala Leu Leu
                20                  25                  30

Xaa Gly Leu
        35

(2) INFORMATION FOR SEQ ID NO: 2:

(i) SEQUENCE CHARACTERISTICS:
    (A) LENGTH: 186 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO: 2:

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
                20                  25                  30

Tyr Asn Gln Thr Val Gln Leu Asp Ile Thr Ala Phe Leu Lys Thr Val
                35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                      70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
                100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Glu Phe Asn Gly Ile Pro Phe Phe Pro Val His
145                 150                 155                 160

Leu Lys Arg Leu Leu Ile Val Val Val Val Val Val Leu Ile Val Val
                165                 170                 175

Val Ile Val Gly Ala Leu Leu Ile Gly Leu
            180                 185

SYNTHETIC PEPTIDE ANALOGS OF LUNG SURFACE PROTEIN SP-C

TECHNICAL FIELD

The invention relates to polypeptides with pulmonary surfactant activity, processes for the preparation thereof and therapeutic compositions containing these.

PRIOR ART

The lungs of all vertebrates contain a mixture of substances which is referred to as "pulmonary surfactant". It has surface-active properties and reduces the surface tension in the alveolar region of the lungs to such an extent that collapse of the terminal regions of the airways on breathing out is avoided. This mixture of substances controls the surface tension in a dynamic manner so that the collapse, which is to be expected according to Laplace's theorem, of the small alveoli in favor of the larger ones is prevented by appropriate adjustment of the surface tension. The result of this is a well-balanced, histologically and physiologically stable structure of the lungs.

Pulmonary surfactant is secreted by the type II alveolar pneumocytes in the form of lamellar bodies. These are compact units of phospholipid bilayers with a high content of dipalmitoylphosphatidylcholine (DPPC) and phosphatidylglycerol (PG). Further essential components present in pulmonary surfactant are proteins referred to as SP-A, SP-B and SP-C. SP-A is a high molecular weight glycoprotein which plays a crucial part in controlling secretion.

The proteins SP-C and, to a smaller extent, SP-B assume the role of "thermodynamic catalysts" in forming the monomolecular surface film (the surfactant in the narrower sense). The presence of these proteins greatly speeds up the kinetics of spreading. Only this makes it possible to adjust, without delay, the surfactant composition to the particular surface tension requirements. These properties are reflected by the extremely hydrophobic nature of the proteins, especially of SP-C.

It has been possible to obtain, by extraction of pulmonary tissue or irrigation of animal lungs, surfactant preparations which show, both in physicochemical measuring equipment, such as in animal models, and on clinical use, the ability to compensate for a surfactant deficiency and thus are suitably, for example, for the treatment of infant respiratory distress syndrome (IRDS). However, these animal preparations have serious intrinsic weaknesses:

The composition of the phospholipids depends greatly on the animal species, health and nutritional state of the animal and can be compensated to only a limited extent by admixture of defined components. The content of surfactant proteins and the SP-B/SP-C ratio is subject to the same uncertainties. An additional factor is that the mixture employed for therapy also contains possible proteolytic breakdown products of the proteins or modified derivatives (for example by oxidation on methionine). On long-term use or administration of large amounts of surfactant as might be necessary, for example, in cases of adult respiratory distress syndrome (shock lung, ARDS) or in other fields of use, such as, for example, the utilization of surfactant as "entrainer" for other substances on pulmonary administration, the question of the supply of substance is open.

It is therefore obvious to solve these problems by preparing the proteins by genetic manipulation. Since recombinant proteins can, especially on use of bacterial expression systems, be prepared in virtually unlimited amounts, and the use of modern analytical methods and quality controls is possible, it is possible by using synthetic phospholipids to prepare a surfactant of exactly defined composition. This can be adjusted optimally to the therapeutic requirements.

The human protein SP-C (see formula I with A=H or Phe, S=Cys and C=Met), which is particularly important for the kinetics of spreading, consists in its central part exclusively of aliphatic, very hydrophobic amino acids such as valine, leucine and isoleucine. The length of this central part (amino acids 12–34) permits the peptide to be integrated into the monomolecular phospholipid film. In the Pro-Cys Cys-Pro sequence (position 3–6), the two Cys residues are thioesterified by palmitic acid on the SH groups. The palmitic acid further increases the hydrophobic nature of the complex protein and, at the same time, blocks the two SH groups of the cysteines and protects them from oxidation and disulfide bridge formation. The central region (amino acids 13–34) forms a transmembrane helix. This region is flanked at the N terminus by a polar sequence which contains positively charged amino acids (Lys, 10; Arg, 11).

WO 91/18015 describes the preparation of recombinant SP-C and of mutants of SP-C. It, is proposed therein, inter alia, to replace the two cysteines in position 4 and 5 by two serines. This has the advantage for the preparation that the technically complicated palmitoylation of the two cysteines after isolation of the very hydrophobic protein is unnecessary.

DESCRIPTION OF THE INVENTION

It has now been found, surprisingly, that SP-C mutants which differ from human SP-C by replacement of the two cysteines in positions 4 and 5 by phenylalanine or tryptophan and replacement of the mechionine in position 32 by isoleucine, leucine or serine show no losses of function whatsoever compared with natural SP-C and are in fact superior to the latter with regard to stability. The genetic engineering preparation is considerably simpler and gives higher yields. The novel polypeptides with pulmonary surfactant activity can be prepared in very high purity.

The invention therefore relates to polypeptides with pulmonary surfactant activity and with an amino-acid sequence (SEQ ID NO:1) according to the general formula I

| 0 | 1 | 2 | 3 | 4 | 5 | 6 | 7 | 8 | 9 | 10 | (I) |
|---|---|---|---|---|---|---|---|---|---|----|-----|
| (A) | Gly | Ile | Pro | B | B | Pro | Val | His | Leu | Lys, | |

| 11 | 12 | 13 | 14 | 15 | 16 | 17 | 18 | 19 | 20 |
|----|----|----|----|----|----|----|----|----|----|
| Arg | Leu | Leu | Ile | Val | Val | Val | Val | Val | Val |

| 21 | 22 | 23 | 24 | 25 | 26 | 27 | 28 | 29 | 30 |
|----|----|----|----|----|----|----|----|----|----|
| Leu | Ile | Val | Val | Val | Ile | Val | Gly | Ala | Leu |

| 31 | 32 | 33 | 34 |
|----|----|----|----|
| Leu | C | Gly | Leu, | in which
A is H or Phe,
B is Phe or Trp and
C is Ile, Leu or Ser.

The invention preferably relates to polypeptides of the general formula I in which A is H or Phe, B is Phe and C is Ile, with the meanings A=H, B=Phe and C=Ile being particularly preferred.

The invention furthermore relates to pharmaceutical compositions which comprises one or more polypeptides according to the invention and, if required, additionally contain one or more polypeptides with pulmonary surfactant activity from the group of SP-A and SP-B, preferably SP-B.

The polypeptides according to the invention can be prepared either by the known methods of solid-phase peptide synthesis or with the aid of appropriate recombinant vectors in host cells. The techniques of constructing vectors, transforming cells, bringing about expression of the protein in the transformed cells and isolating and purifying the expressed proteins are known per se to the skilled worker (for example WO 86/03408, WO 87/06588 and WO 91/18015). The preparation of vectors for expressing SP-C in bacterial systems has recourse to conventional methods of recombinant DNA technology.

It is possible to express the hydrophobic SP-C protein in bacteria in large amount and without harming the host cell only in the form of suitable fusion proteins such as, for example, together with chloramphenicol acetyltransferase (CAT). For example, the vector pTrpAmpCAT152 codes for the N-terminal region of CAT and provides a (5')EcoR1 and a (3')Patl cleavage site for the in-frame cloning of DNA fragments which code for SP-C. CAT and SP-C are in this case connected together at the protein level via a hydroxylamine-sensitive point of fusion (AsN↓Gly). Vectors of this type such as pTrpAmpCAT152::SPC, permit controlled expression of the corresponding fusion proteins up to the production scale (fermentation). Expression of the fusion proteins causes the formation of inclusion bodies in the host cell. It is moreover possible to alter the length of the CAT portion in the fusion protein so that high yields of inclusion bodies with a high SP-C content are obtained.

Expression can take place not only in bacteria but also in a large number of host systems such as, for example, in mammalian, yeast and insect cells. The DNA constructs suitable for the various host cells are synthesized by known methods and incorporated into the genome of the host cells with appropriate control sequences in a conventional way.

The DNA olignonucleotides can be synthesized by the conventional phosphoamidite method in a MilliGen/Biosearch Cyclone DNA synthesizer.

The first DNA oligonucleotide forms the sense strand of the DNA with a length of 118 nucleotides. This codes (in the 5'→3' direction) for an Eco R1-specific 5' and for subsequent subcloning, the Asn/Gly hydroxylamine cleavage site a-d the human SP-C starting with Gly-25 and ending with Leu-58 of the SP-C precursor sequence, corresponding to Gly-1 and Leu-34, respectively, in formula I. This entailed the known amino-acid sequence of the human SP-C protein being translated into DNA in accordance with the rules of the genetic code. However, the sequence is modified so that the two cysteines in position 28 and 29 of the SP-C precursor sequence are replaced by phenylalanines or by tryptophans and the methionine in position 56 of the precursor protein sequence is replaced by isoleucine, leucine or serine. It is additionally possible in this way to take account of the codon usage frequencies of the host cells. A modified SP-C sequence which contains phenylalanine at positions 4 and 5 and isoleucine in position 32 (numbering according to formula I) is referred, in accordance with the usual single-letter code for these two amino acids, to as SPC34 (FF/I). In addition, the sense strand of the DNA contains a TAA stop codon to terminate ribosomal translation, and a Pst 1-specific 3' end. The second DNA oligonucleotide represents the complementary, noncoding (antisense) strand consisting of 110 nucleotides.

The synthetically prepared SP-C DNA fragment is cloned into a suitably expression vector such as, for example, pTrpAmpCAT152. This vector is composed of pKK233 (Pharmacia) which contains an ampicillin resistance gene and is a derivative of pBR322. The trc promoter can be replaced by a trp promoter, as in pTrpAmpCAT152. It is likewise possible to employ other inducible promoters.

For subcloning of the SP-C fragment, the complementary DNA oligonucleotides are initially hybridized together. The DNA double strand resulting therefrom has protruding single-stranded ends (Eco R1/Pst1).

Incorporation into the vector DNA takes place in a conventional way after Eco R1/Pst 1 digestion of the vector DNA, purification of the required vector DNA fragment by agarose gel electrophoresis and by hybridization of the SP-C DNA and of the vector fragment via the cohesive ends. Subsequently the two fragments are covalently linked together by ligation by known methods.

For DNA amplification and plasmid isolation, conventional protocols are used, for example, for transformation into calcium chloride-competent $E.$ $coli$ MM294 cells and, for selection of plasmid-harboring cells, plating on LB agar plates with ampicillin. Plasmid DNA is isolated from the resulting Amp-resistant colonies and is analyzed with suitable combinations of restriction enzymes. Clones with the expected DNA restriction fragment pattern are selected. Complete sequencing of the plasmid sequence confirms correct insertion of the SPC34 (FF/I) sequence.

The plasmid vectors obtained in this way permit expression of the fusion protein CAT::SPC under control of the Trp promoter (or other promoters). The recombinant fusion protein is produced n the form of inclusion bodies in the host cells after induction.

The fusion protein CAT152:SPC34 (FF/I) has the amino acid sequence shown in SEQ ID NO: 2. Residues 153 to 186 of SEQ ID NO: 2 correspond to residues 1 to 34 of the SP-C(FF/I) peptide.

Subsequent cleavage with hydroxylamine to separate CAT and SP-C takes place between Asn-152 and Gly-153 (corresponds to the 1st amino acid in the SP-C peptide). The SP-C peptide is removed and purified by methods customary in protein chemistry.

The polypeptides according to the invention can be made available singly or in combination with one another in pharmaceutical compositions which are adjusted to the requirements of airway treatment. The compositions are suitable not only for treatment of respiratory distress syndrome in premature babies and adults but also for treatment of pneumonia and bronchitis. The polypeptides according to the invention are also suitable as entrainers for medicinal substances which can be administered by inhalation.

Besides the polypeptides, the compositions contain phospholipids, preferably those phospholipids which are present in natural pulmonary surfactant compositions, such as, preferably, dipalmitoylphosphatidylcholine (DPPC), palmitoyloleylphosphatidylglycerol (POPG) and/or phosphatidylglycerol (PG). The compositions contain calcium or magnesium ions and sodium chloride to set a favorable viscosity. The skilled worker will base has determination of the type and amount of the individual constituents of the composition on the one hand on the known composition of natural pulmonary surfactant, and on the other hand on the numerous proposals in the prior art, such as, for example, EP-A 0119056 and EP-A 0406732.

Preferred compositions according to the invention contain 80 to 95% by weight of phospholipids, 0.5 to 3.0% by weight of polypeptides, 4 to 7% by weight of fatty acid, preferably palmitic acid, and 1 to 3% by weight of calcium chloride.

PREPARATION EXAMPLE

1. Producer strain

The producer strain *E. coli* 199 which was used is derived from the *E. coli* K12 strain MM294 which can be purchased under No. 5208 from the Deutsche Sammlung von Mikroorganismen and Zelikulturen GmbH (DSM, Braunschweig).

The expression vector pTrpAmpCAT152::SPC34 (FF/I) containing the gene for the fusion protein CAT152::SPC34 (FF/I) was derived from the DNA sequence pBR322, a ColE1 derivative (E. Weber (ed.) (1988), Biologische Sicherbeit, Bundesministerium Für Forschung and Technologie, Bonn). the Trc promoter was cut out of the plasmid pKK233-2, which can be obtained from Pharmacia with Eco R1/Hind 3 and was replaced by a synthetic Trp promoter (pTrp233). The latter consists of the promoter region (binding site for RNA polymerase), the operator region (binding site for the Trp repressor), a Shine/Dalgarno (S/D) sequence and restriction sites for cloning. The gene (CAT152) coding for the 152 amino acids of the 5'part of the bacterial chloramphenicol acetyltransferase was inserted behind the Trp promoter. A synthetic gene fragment which codes for the 34 amino acids of the human-like SP-C(FF/I) was fused to the CAT152 DNA partial sequence. The functional CAT::SPC(FF/I) transcription unit is completed by the bacterial rrnB transcription terminator sequence T1T2. The resulting construct is referred to as pTrpAmpCAT152:: SPC34 (FF/I).

The vector pTrpAmpCAT152::SPC34 (FF/I) has the following functional elements:

CAT152::SPC34(FF/I) gene controlled by Trp promoter and T1T2 transcription terminator;

ori region and adjacent regions, via which the copy number of the plasmid is controlled;

Amp_ gene

After the plasmid has been introduced into the host cell, the latter has a high copy number of the Trp promoter-controlled CAT::SPC(FF/I) gene. The trp repressor is provided by the host cell itself.

The obtaining of rCAT::SPC by fermentation is controlled via the concentration of tryptophan in the medium or via addition of β-IAA (β-indolylacrylic acid).

3. Batch fermentation

Culture medium (see below for composition) in a shaken flask is inoculated (1 1 preculture or starter culture) with a sample tube of the working cell bank (glycerol culture) and incubated under strong ampicillin selection pressure at 37° C. with shaking. The growth is monitored via the optical density at 578 nm. When the *E. coli* 199 starter culture reaches an optical density of more than 3, the culture is used to inoculate a 10 l fermenter, and growth of the bacteria is continued under reduced ampicillin selection pressure. As soon as the optical density has reached a value between 5 and 6, and 10 l culture is transferred into a 100 l fermenter and incubated further under the same conditions. After sufficient growth, the Trp promoter-controlled CAT::SPC (FF/I) transcription unit is induced by adding, for example, 40 ml/l β-IAA. After induction, fermentation is continued for 4–5 hours unit the cells are harvested.

During the fermentation, the partial pressure of oxygen ($pO_2$), pH and temperature of the fermentation broth are measured and controlled on-line. The pH is kept constant with sodium hydroxide solution, and the partial pressure of oxygen ($pO_2$) is controlled via the input of oxygen and the stirrer speed. Determination of the optical density of 578 nm and of the concentration of the C source in the medium takes place off-line. Foam formation is detected with a foam sensor, through which antifoam agent can be metered in where appropriate to control the foam.

Aliquots of the culture broth are taken at various times. After lysis of the bacteria, the expression is checked by fractionating, and staining, the *E. coli* proteins on a polyacrylamide gel. The percentage content of the (predominant) proteins in the total *E. coli* protein is determined by densitometry. Shortly after induction of the recombination gene, a new predominant protein band appears (rCAT::SPC). The culture medium has the following composition: soybean peptone 27.0 g/l, yeast autolyzate KAV 14.0 g/l, NaCl 5.0 g/l, $K_2HPO_4 \times 3\ H_2O$ 6.0 g/l, $KH_2PO_4$ 3.0 g/l, $MgSO_4 \times 7\ H_2O$ 0.5 g/l, glycerol (99.5% pure) 30.0 g/l, antifoam J673 (Struktol Comp.) 0.2 ml/l, L-tryptophan 80.0 mg/l and ampicillin 20 mg/l for the 1 st preculture and 5 mg/l for the 2nd preculture and the 100 l fermenter.

Before the autoclaving and sterilizing of the complex nutrient medium, the pH is adjusted to pH 6.8 with 2N NaOH. Used for the preculture in the 10 l fermenter is a stirring speed of 750 rpm and an air input of 10 l/min at 37° C., and for the main culture in the 100 l fermenter is a stirring speed of 400 rpm and an air input of 70 l/min at 37° C. Antifoam is added as required with a disposable syringe through a septum.

About 4 hours after induction, the cells are removed from the culture broth by filtration and/or centrifugation. The moist biomass is collected in a stainless steel container and stirred with 10 l of disruption buffer (pH 8.0) in a cold room overnight (4° C., 16 hours). The stirred cell suspension is disrupted (room temperature) in a high-pressure homogenizer ($\leq 700$ bar) and again collected in a sterile stainless steel container. The inclusion bodies are subsequently harvested immediately by filtration and/or centrifugation (Sorvall RC2-B centrifuge, 27,000 g) at 4° C., resuspended in buffer (about 1 l) and, for example, transferred in portions of about 350 ml into 1 round-bottom flasks and lyophilized for about 96 hours. About 200 g of dry inclusion bodies containing more than 20% by weight of fusion protein are obtained from a 100 l fermentation. The lyophilized inclusion bodies can be stored at −20° C. for some months.

3. Cleavage of the fusion protein and purification of the lipophilic peptide SP-C(FF/I)

100 g of dry inclusion bodies are dissolved in 1.6 l of 8 molar guanidine hydrochloride solution (917.1 g), heating gently. Undissolved residues are removed by filtration through a fluted filter. To cleave the fusion protein at the Asn-Gly connection point, 167 g of hydroxylammonium chloride are added to the solution, and the pH of the solution is adjusted to 9.6 with 2N NaOH. The cleavage solution is then left to stand with stirring at room temperature for 3–4 days. At the end of the reaction time, SP-C(FF/I) is precipitated by adding 6.4 l of the tris buffer (pH 8.0) and is sedimented with the aid of a centrifuge (Servall RC2-b centrifuge, 20,000 g). The supernatant is decanted off, and the SPC pellet is resuspended in 400–500 ml of tris buffer and centrifuged again under the same conditions for 30 minutes.

The SP-C pellet is taken up in 3.5 l of a chloroform/methanol mixture containing hydrochloric acid (1.75 l of $CHCl_3$+1.75 l of $CH_3OH$+ about 30 ml of 2N HCl). This crude SP-C solution is further purified by preparative HPLC on C8 reverse phase material. The chloroform/methanol extract is, before application to the preparative HPLC column, diluted with 90% strength methanol in the ratio of about 1:2. It is possible with this solution to load, for example, a column (diameter 5 cm) with about 400 mg of SP-C (FF/I) (for example with ~2 l of diluted crude extract). The SP-C (FF/I) is eluted under acidic conditions (pH 2–3)

with a water/i-propanol gradient (see separation conditions). After chromatography for about 30 minutes, 4–6 fractions of 200 ml are collected in the region in which the SP-C elutes (UV detection at 220 nm). The fractions are checked by analytical HPLC and pooled appropriately. If the samples are stored, they are frozen in liquid nitrogen and kept in a deepfreeze at −80° C. SP-C(FF/I) is obtained in a purity of 98.5–99.5%.

Separation conditions:

| Column | Kromasil C8 100 A 16 μm 300 mm * 50 mm I.D. | | | | |
|---|---|---|---|---|---|
| Eluent | A: HPLC water from Millipore system B: i-PrOH linear gradient C: 60 mmol/l HCl (dilution of fuming hydrochloric acid) | | | | |
| Gradient: | Time | % A | % B | % C | Flow rate [ml/min] |
|  | 0 | 45 | 50 | 5 | 100 |
|  | 10 | 45 | 50 | 5 | 100 |
|  | 55 | 0 | 95 | 5 | 100 |
|  | 65 | 0 | 95 | 5 | 100 |
|  | 75 | 45 | 50 | 5 | 100 |
|  | 85 | 45 | 50 | 5 | 100 |
|  | 90 | 45 | 50 | 5 | 0.2 |

4. Incorporation of SP-C(FF/I) into a phospholipid matrix

The lipophilic peptide SP-C(FF/I) is mixed in solution in i-propanol with the components of the phospholipid matrix and precipitated in a homogeneous mixture with the components of the phospholipid matrix by spraying into a dilute sodium chloride solution (0.06% w/w NaCl) at room temperature. The LSF is removed from the pulmonary surfactant suspension using a bowl centrifuge, and is resuspended in electrolyte solution. (NaCl, $CaCl_2$), and the pH is adjusted to pH 6.5 with 0.1N. This aqueous suspension is dispensed into 20 ml vials and lyophilized. The weights and volume stated in the following preparation example relate to the preparation of 10 g of pulmonary surfactact preparation.

7.00 g of dipalmitoylphosphatidylcholine (DPPC), 3.08 g of palmitoyloleylphosphatidylglycerol ammonium salt (PDPG×$NH_4$) and 0.25 g of palmitic acid are dissolved at 40° C. in 200 ml of 90% i-propanol and then cooled to room temperature. The resulting phospholipid solution is combined with 1 l of a solution which contains 200 mg of purified SP-C(FF/I) and has been obtained from the HPLC purification. The resulting "spray solution" is adjusted to pH 4.5 by stirring with bicarbonate solution (about 5 ml of 5% $NaHCO_3$ solution).

The "spray solution" is introduced at room temperature at a spraying rate of 25 ml/min through a single component nozzle into 9.6 l of dilute NaCl solution (0.065% w/w) while stirring vigorously. An opalescent solution forms and, after storage at 4°–8° C. for 2 hours, the pulmonary surfactant preparation is precipitated by spraying in an electrolyte solution (3.0 g of $CaCl_2 \times 2\ H_2O$ and 61.3 g of NaCl in 300 ml of $H_2O$). The pulmonary surfactant suspension (total volume 10.8–11.0 l) is stored at 4° C. overnight and then centrifuged with a Sorvall bowl centrifuge (RC2-B) at 16,000 g for 30 minutes in each case. The centrifugation pellet is in each case resuspended in half the volume of 0.65% strength sodium chloride solution and centrifuged again to remove adherent residues of i-propanol. This procedure is repeated a total of 3–4 times. The pellet from the last centrifugation is taken up to 400 ml of 0.65% strength NaCl solution, adjusted to pH 6.5 with 0.1N NaOH and divided into portions of 6.2 g in 20 ml vials. The content of the vials is lyophilized as follows: freezing at −45° C. for 6 hours under atmospheric pressure, freeze drying at −20° C. under 0.16 mbar for 54 hours and than at −20° C. under 0.02 mbar for 5 hours for further intensive drying.

65–66 vials each of which contains 0.150 g of pulmonary surfactant (calculated without NaCl) are obtained.

The dry pulmonary surfactant samples are stored in a refrigerator at 4° C. and must be resuspended with water or physiological sodium chloride solution before use (suspension concentration 25 mg/ml). Each vial contains:
95.6 mg of dipalmitoylphosphatidylcholine
42.1 mg of palmitoyloleylphosphatidylglycerol (ammonium salt;
2.7 mg of SP-C(FF/I)
6.8 mg of palmitic acid
2.9 mg of calcium chloride (anhydrous)

We claim:

1. A polypeptide with pulmonary surfactant activity having the amino acid sequence shown in SEQ ID NO: 1, wherein
  Xaa at position 1 is Phe or is absent;
  Xaa at positions 5 and 6 are both Phe or both Trp; and
  Xaa at position 33 is Ile, Leu, or Ser.

2. A polypeptide according to claim 1, wherein $Xaa^1$ is Phe or is absent, $Xaa^5$ and $Xaa^6$ are both Phe, and $Xaa^{33}$ is Ile.

3. A polypeptide according to claim 2, wherein $Xaa^1$ is Phe.

4. A polypeptide according to claim 2, wherein $Xaa^1$ is absent.

5. A pharmaceutical composition comprising an amount of a polypeptide according to claim 1 effective to treat respiratory distress syndrome (RDS) in a mammal and a pharmaceutically acceptable carrier or excipient.

6. A pharmaceutical composition according to claim 5, wherein $Xaa^1$ is absent.

7. A pharmaceutical composition according to claim 5, further comprising one or both of pulmonary surfactant polypeptides SP-A and SP-B.

8. A pharmaceutical composition according to claim 7 comprising SP-B.

9. A pharmaceutical composition according to claim 5, further comprising one or more phospholipids.

10. A pharmaceutical composition according to claim 9, comprising a phospholipid selected from the group consisting of dipalmitoylphosphatidylcholine (DPPC), palmitoyloleylphosphatidylglycerol (POPG), and phosphaticylglycerol (PG).

11. A pharmaceutical composition according to claim 9 comprising palmitic acid and further comprising an electrolyte.

12. A pharmaceutical composition according to claim 11 wherein the electrolyte is a sodium salt, a calcium salt, or a mixed sodium/calcium salt.

\* \* \* \* \*